(12) United States Patent
Huang

(10) Patent No.: US 8,728,298 B2
(45) Date of Patent: May 20, 2014

(54) TEST METHOD FOR THE KETONE NUMBER OF AN ANIMAL SPECIMEN

(75) Inventor: Tong-Yuh Huang, Hsin-chu County (TW)

(73) Assignee: Sand County Biotechnology, Inc., Hu-Ko, Hsin-Chu County (TW)

( * ) Notice: Subject to any disclaimer, the term of this patent is extended or adjusted under 35 U.S.C. 154(b) by 189 days.

(21) Appl. No.: 13/352,877

(22) Filed: Jan. 18, 2012

(65) Prior Publication Data

US 2013/0180868 A1    Jul. 18, 2013

(51) Int. Cl.
*G01N 27/327* (2006.01)

(52) U.S. Cl.
USPC .......................................... 205/792; 205/775

(58) Field of Classification Search
USPC ............. 204/403.01–403.15; 205/777.5, 778, 205/792
See application file for complete search history.

(56) References Cited

U.S. PATENT DOCUMENTS

| | | | | |
|---|---|---|---|---|
| 5,266,179 | A * | 11/1993 | Nankai et al. | 204/401 |
| 6,413,213 | B1 * | 7/2002 | Essenpreis et al. | 600/300 |
| 6,635,167 | B1 * | 10/2003 | Batman et al. | 205/775 |
| 6,984,307 | B2 * | 1/2006 | Zweig | 205/777.5 |

OTHER PUBLICATIONS

Abbott product brochure for AlphaTRAK™, published Mar. 2006.*
Cozzi et al. Clinical Evaluation of the Hand-Held Abbott AlphaTRAK™ Blood Glucose Monitoring System for Use with Dog and Cat Blood Samples, published Feb. 2006, provided as a hyperlink "Download Clinical Trial" at the end of AlphaTRAK brochure.*
Rucinsky et al. "AAHA Diabetes Management Guidelines for Dogs and Cats," Journal of the American Hospital Association 2010, 46:215-214.*
Batchelor et al., "Amperometric Assay for the Ketone Body 3-Hydroxybutyrate," Analytica Chimica Acta, 221 (1989) 289-294.*
Brochure entitled "Blood Glucose Monitoring System for Dog & Cat," produced by Ceragem Medisys, which to the Examiner's best knowledge was published in 2012 and is not paginated.*

* cited by examiner

*Primary Examiner* — Alex Noguerola
(74) *Attorney, Agent, or Firm* — Egbert Law Offices, PLLC

(57) ABSTRACT

A test method for the ketone number of an animal specimen is characterized in that a test parameter datasheet is set up by data modeling. Then a specimen from tested animal body is obtained. Next, the specimen is dripped onto the sensing end of an electrochemical test specimen, and an electrochemical tester is prepared. A test value correction procedure is built into or input to the electrochemical tester. With a parameter adjustment mode, the operational parameters of test value correction procedure unique to the electrochemical tester could be adjusted for adapting to the test mode of the species of tested animals. The sensing end of the electrochemical test specimen is inserted into the measurement slot of the electrochemical tester, so the ketone number of the specimen is displayed by the electrochemical tester.

9 Claims, 8 Drawing Sheets

TEST METHOD FOR THE KETONE NUMBER OF AN ANIMAL SPECIMEN

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates generally to a test method, and more particularly to an innovative one which is used to test the ketone number of an animal specimen.

2. Description of Related Art Including Information Disclosed Under 37 CFR 1.97 and 37 CFR 1.98.

A kind of "ketosis" may occur when the energy contained in domestic animals is under a negative balance state. Where dairy cattle is concerned, such ketosis generally occurs in the early stage of lactation, when the feed intake of dairy cattle cannot meet the growing demand for lactation. In such a case, dairy cattle will start to turn in-vivo fat into the energy source. Of which, the liver is an organ for energy conversion. However, only limited fat could be converted into useable energy (i.e.: glucose). In the case of overload, the liver may generate ketone, which could be used as an energy source with lower efficiency, leading to discomfort of dairy cattle, even malignant pathological changes and finally the so-called "clinical ketosis".

In the event of occurrence of ketosis, all dairy cattle in the same breeding region will be possibly affected, resulting in substantial economic loss for the stock farmers. Hence, there is an important and urgent task to prevent the occurrence and spreading of ketosis.

Some common solutions are already adopted in this field. Among which, one solution is to test ketosis using uranalysis, but this simple method has poor accuracy despite of low cost, since the content of blood ketone could not be accurately estimated through the color change of urine. Hence, such a method is only suited for a general survey of cattle. Another solution is to test blood ketone using the test method of β-Hydroxybutyric Acid (BHBA). Notwithstanding higher accuracy, this solution cannot be accomplished by farmers, so professional veterinarians are often required to extract blood from the animal bodies, and then take the blood back to medical institutions or labs for chemical examination. However, since the test process is subject to professional veterinarians, such method lacks of flexibility and working efficiency, meanwhile the test by professional veterinarians is of a very high cost, increasing the burden of the farmers with poor economic benefits.

Currently, a specimen is available to test the ketone number of human bodies in collaboration with a testing machine. Yet, such a specimen cannot be used directly to test the ketone number of animals due to different blood concentrations and contents of the human and animal bodies. Furthermore, the test value of animals' ketone number with the specimen is unhelpful to accurate identification and judgment.

Thus, to overcome the aforementioned problems of the prior art, it would be an advancement if the art to provide an improved structure that can significantly improve the efficacy.

Therefore, the inventor has provided the present invention of practicability after deliberate design and evaluation based on years of experience in the production, development and design of related products.

BRIEF SUMMARY OF THE INVENTION

Based on the unique design of the present invention wherein the "test method for ketone number of animal specimen" allows to test the specimen of tested animals by said electrochemical tester through electrochemical test specimen, and adjust the operational parameters of the test value correction procedure of the electrochemical tester by said parameter adjustment mode for adapting to the test mode of the species of tested animals, the present invention enables one to obtain the accuracy degree of the ketone number of the electrochemical tester by the parameter adjustment mode in consistency with or close to special lab tests. The method also saves greatly the procurement and operation cost of said electrochemical test specimen and tester. Moreover, the animal farmers could conduct tests easily and independently. So, the novel test method of the present invention for ketone number of animal specimen enables accurate, low-cost and convenient testing of animal blood ketone with improved applicability.

Although the invention has been explained in relation to its preferred embodiment, it is to be understood that many other possible modifications and variations can be made without departing from the spirit and scope of the invention as hereinafter claimed.

DETAILED DESCRIPTION OF THE INVENTION

FIGS. 1-4 depict preferred embodiments of the test method of the present invention for testing the ketone number of an animal specimen, which, however, are provided for only explanatory objective for patent claims. Said test method for ketone number of animal specimen comprises of the following steps.

Figure 1:
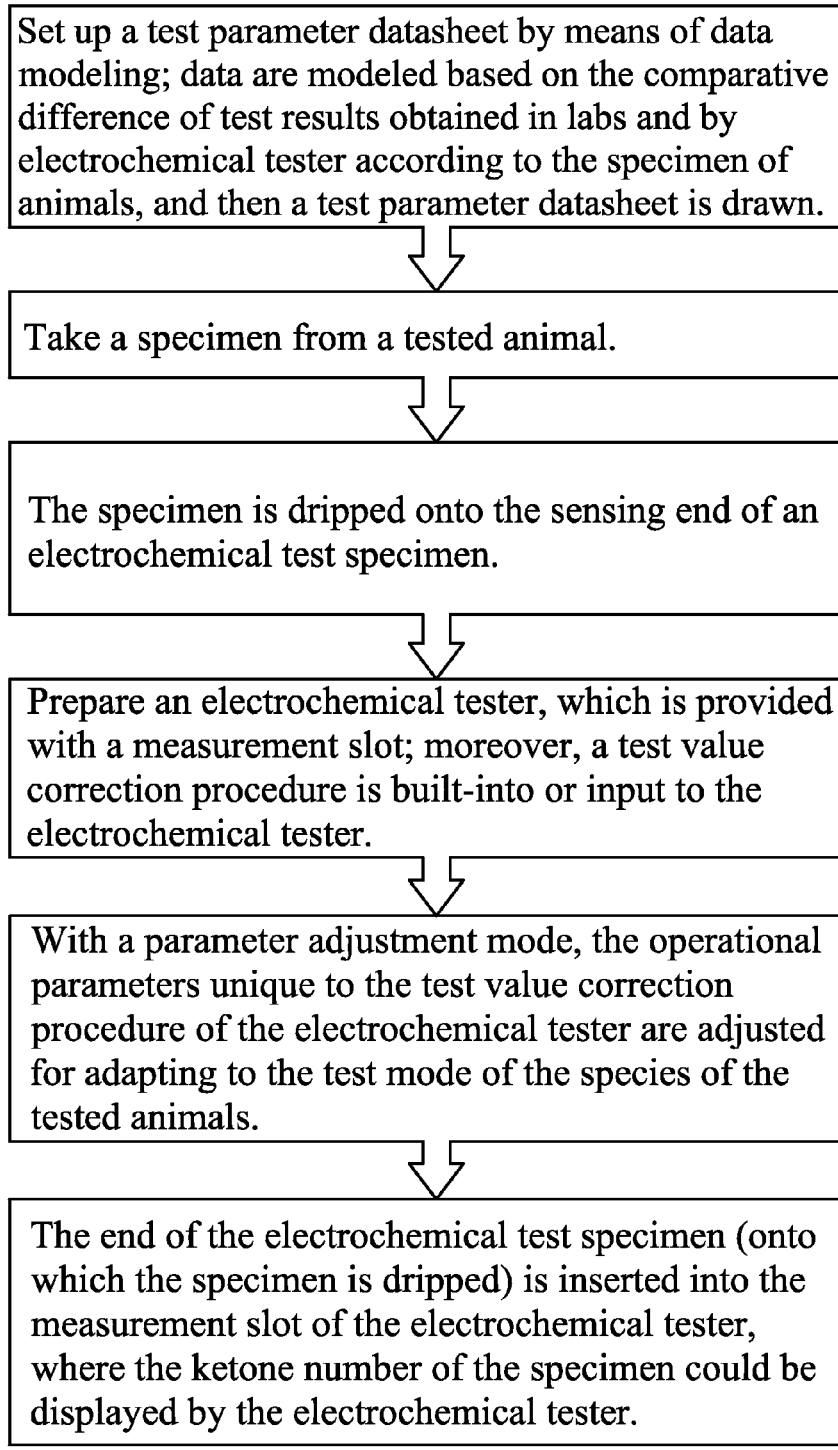
FIG. 1 is a letter block diagram for the test method of the present invention for testing the ketone number of animal specimens.
Figure 2:
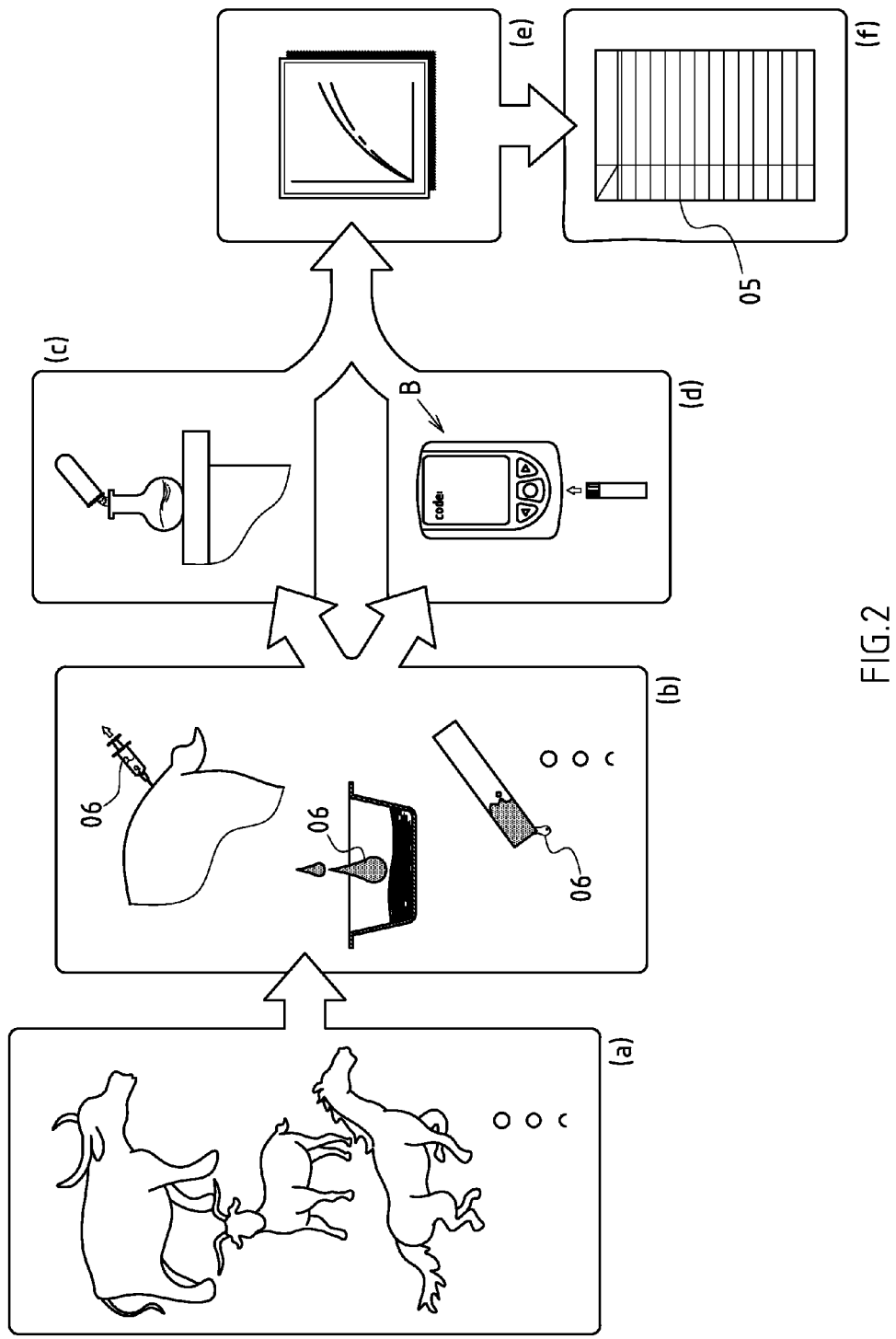
FIG. 2 is an abridged view of the present invention showing the steps of data modeling.

First, referring to FIGS. 1 and 2, set up a test parameter datasheet 05 by means of data modeling. As illustrated in FIG. 2, data are modeled based on the comparative difference of test results (shown by curve in FIG. 2 (e)) obtained in labs (shown by FIG. 2 (c)) and by electrochemical tester B (shown by FIG. 2 (d)) according to the specimen 06 of such animals as: cattle, horse and sheep (shown by FIG. 2 (a)). Then a test parameter datasheet 05 (shown by FIG. 2 (f)) is drawn. Said specimen 06 of animals includes either of blood, body fluid, urine, saliva, tissue fluid, lymph and milk.

Figure 3:
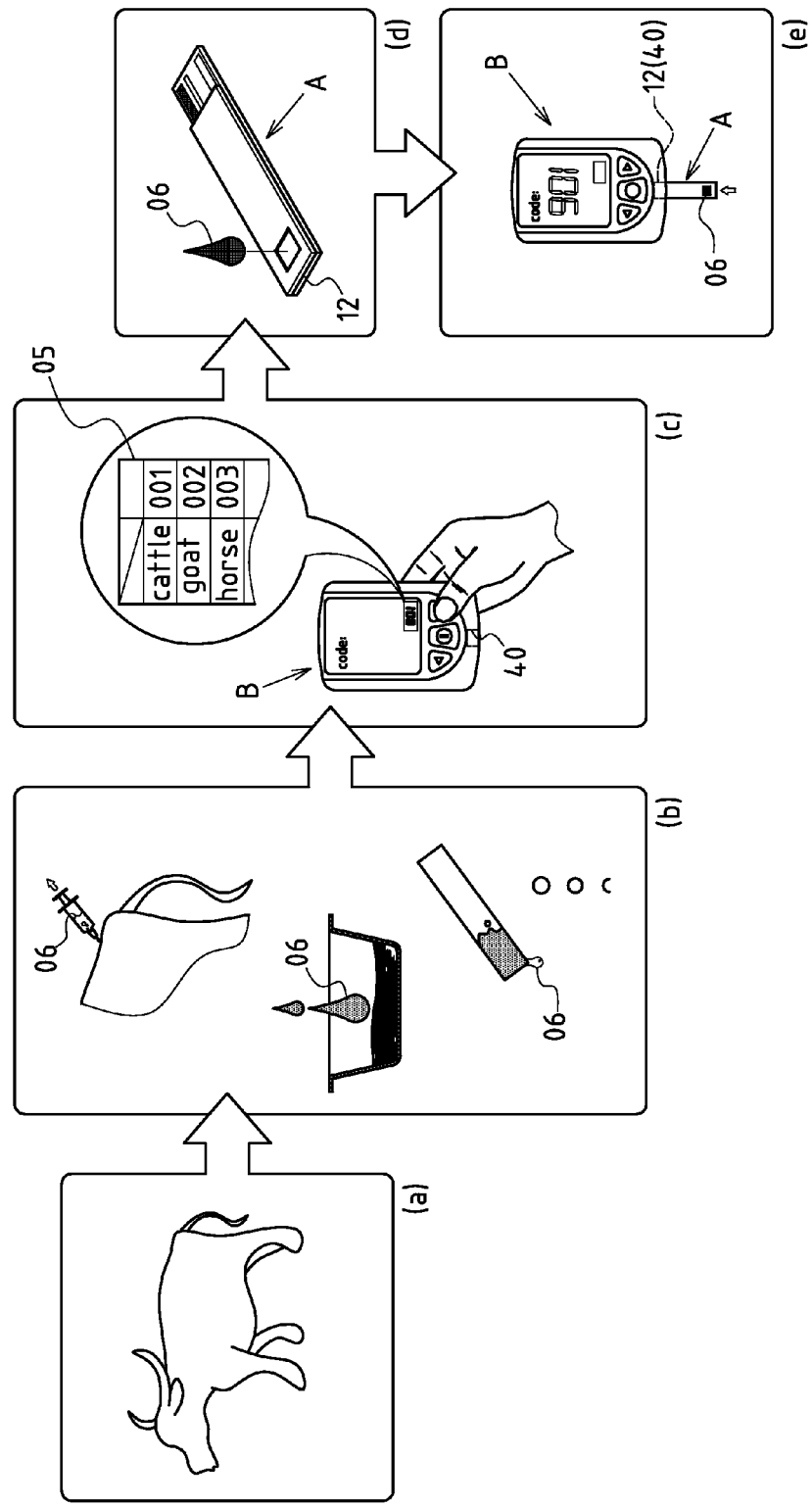
FIG. 3 is an abridged view of the present invention showing the test method for ketone number of an animal specimen.

Second, referring to FIGS. 1 and 3, take a specimen 06 from a tested animal (e.g.: a cattle shown in FIG. 3 (a)) in different ways. As illustrated in FIGS. 2, 3 (b), the blood specimen is obtained by extraction or acupuncture, while the urine and saliva, etc, are obtained by collection or sampling.

Third, referring to FIG. 3 (c), prepare an electrochemical tester B, which is provided with a measurement slot 40. Moreover, a test value correction procedure is built-into or input to the electrochemical tester B.

Fourth, with a parameter adjustment mode, the operational parameters unique to the test value correction procedure of the electrochemical tester B are adjusted for adapting to the test mode of the species of the tested animals. Of which, said test value correction procedure is expressed as: $y=ax+b$, where $x$, $y$ represent separately two axial directions in the curve graph of the ketone number, and $a$, $b$ represent two parameters affecting the curve. Of which, $a$ and $b$ are obtained from the data in said test parameter datasheet 05 (shown in FIG. 3 (C)). Said test parameter datasheet 05 could be prepared into either of cards, electronic codes or electronic files depending on the adjustment modes.

Fifth, referring to FIG. 3 (d), the specimen 06 is dripped onto the sensing end 12 of an electrochemical test specimen A.

Finally, referring to FIG. 3(e), the sensing end 12 of the electrochemical test specimen A (onto which the specimen 06 is dripped) is inserted into the measurement slot 40 of the electrochemical tester B, where the ketone number of the specimen 06 could be displayed by the electrochemical tester B.

With the aforementioned method, the ketone number displayed by the electrochemical tester B has the accuracy degree in consistency with or close to the experimental testing.

Of which, the tested animals are either herbivorous animals such as cattle, sheep or horse, or omnivorous animals such as dog, cat and pig. Also, the tested animals could be categorized into newborn, small and big animals, so different operational parameters could be adjusted to obtain more accurate test result about blood ketone. As for the attributes of the animals, the blood concentration may vary in different stages of their life span, making it unsuitable for the same test standard.

Figure 4:
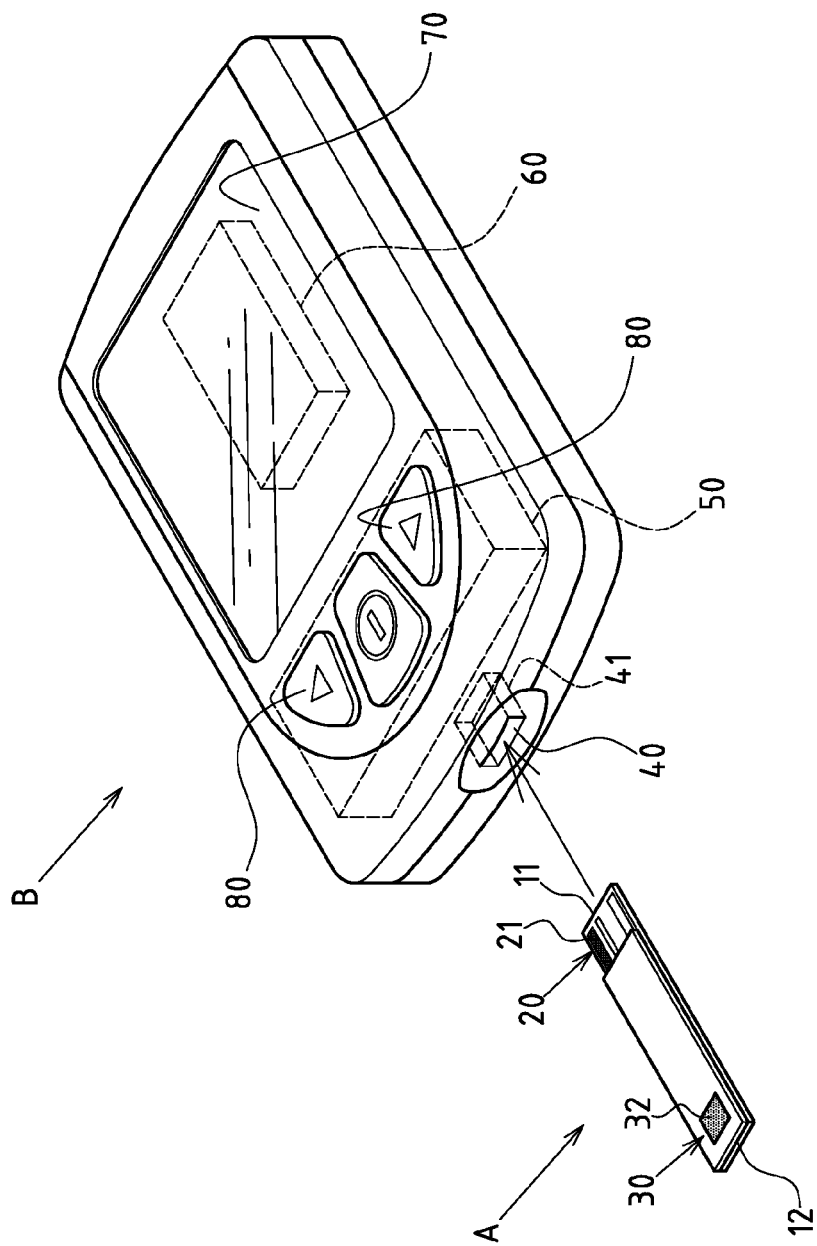
FIG. 4 is a perspective view of the present invention showing the operation mode of the electrochemical test specimen and electrochemical tester.
Figure 5:
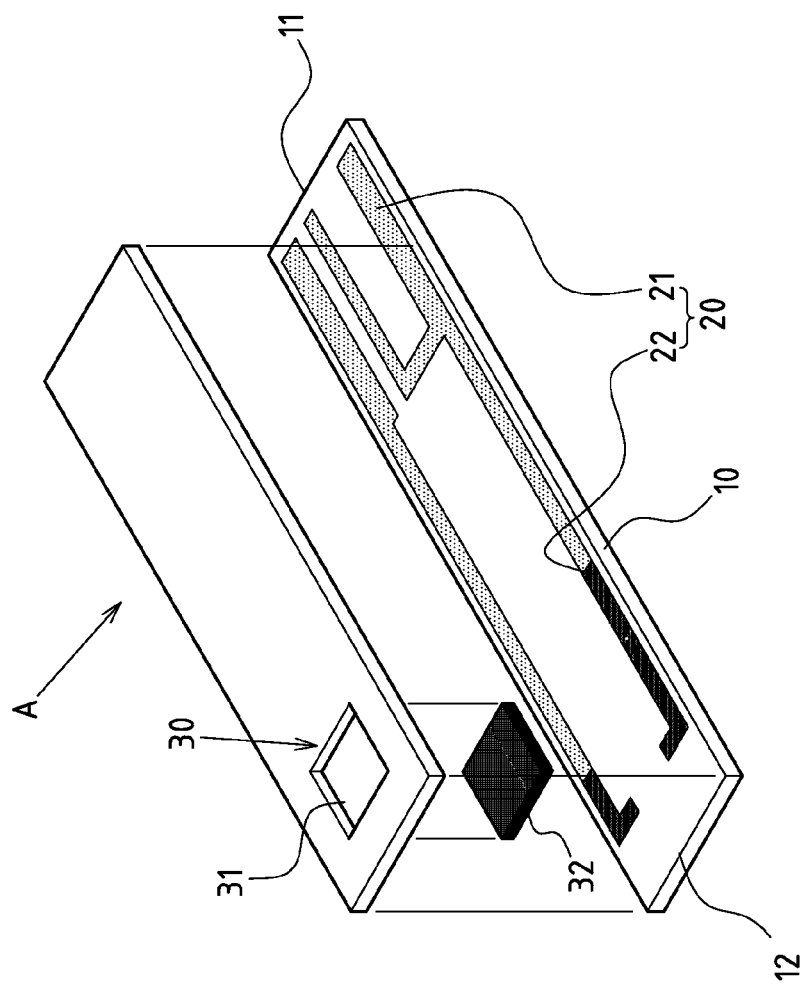
FIG. 5 is an exploded structural view of the electrochemical test specimen of the present invention.

Referring to FIG. 5, said electrochemical test specimen A structurally comprises of a laminar insulation substrate 10, with an insertion end 11 and a sensing end 12. An electrode unit 20 has a detection zone 21 and a reaction zone 22. The detection zone 21 is set correspondingly to the insertion end 11 of the laminar insulation substrate 10, and the reaction zone 22 set correspondingly to the sensing end 12 of the laminar insulation substrate 10. A reaction portion 30 is set at the sensing end 12 of the laminar insulation substrate 10 correspondingly to the reaction zone 22 of the electrode unit 20. Moreover, the reaction portion 30 is provided with a specimen inlet 31 and a chemical reaction zone 32. Referring to FIG. 4, said electrochemical tester B comprises of: a measurement slot 40, used for inserting the insertion end 11 of the electrochemical test specimen A; a voltage generator 50, used to generate a preset voltage; a detection processor 60, used to detect the current signals generated by the electrochemical test specimen A containing said specimen 06 (marked in FIG. 3) within a certain period of time, and correlate the current signals with the concentration of said specimen 06 (marked in FIG. 3); a measurement display 70, used to display specifically the measurement results of the tester.

Figure 6:
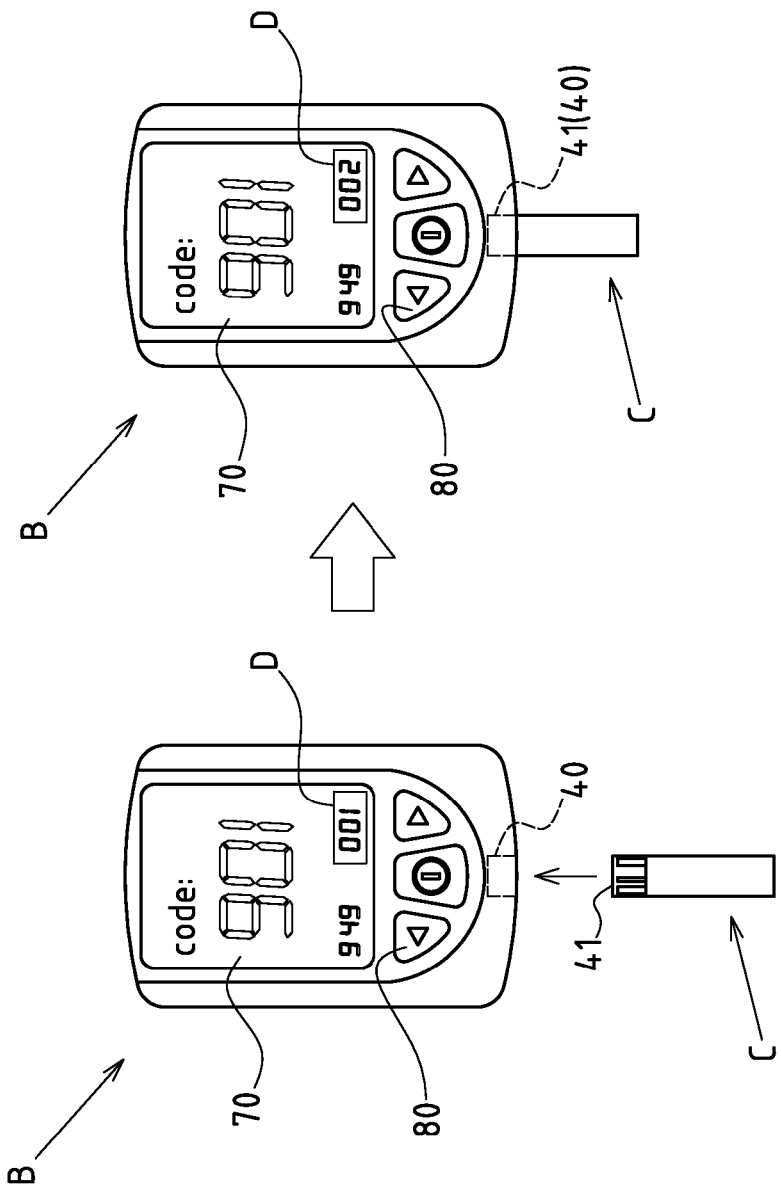
FIG. 6 is a schematic view of the preferred embodiment of the present invention with use of adjustment specimen by test value adjustment mode.

Referring to FIG. 6, said test value adjustment mode could be implemented by an adjustment specimen C, which can be inserted into an insertion portion 41 of the measurement slot 40 set on the electrochemical tester B. An adjustment code is built into the adjustment specimen C, such that the adjustment code can be read when the adjustment specimen C is inserted into the electrochemical tester B, so as to change the operational parameters of the test value correction procedure. As shown by the symbolic letters of a parameter frame D in the measurement display 70 of the electrochemical tester B, after correction of test value by the adjustment specimen C, the symbolic letters shown by a parameter frame D in the electrochemical tester B are switched to the symbolic letters represented by the adjustment code of adjustment specimen C unique to the tested animal.

Figure 7:
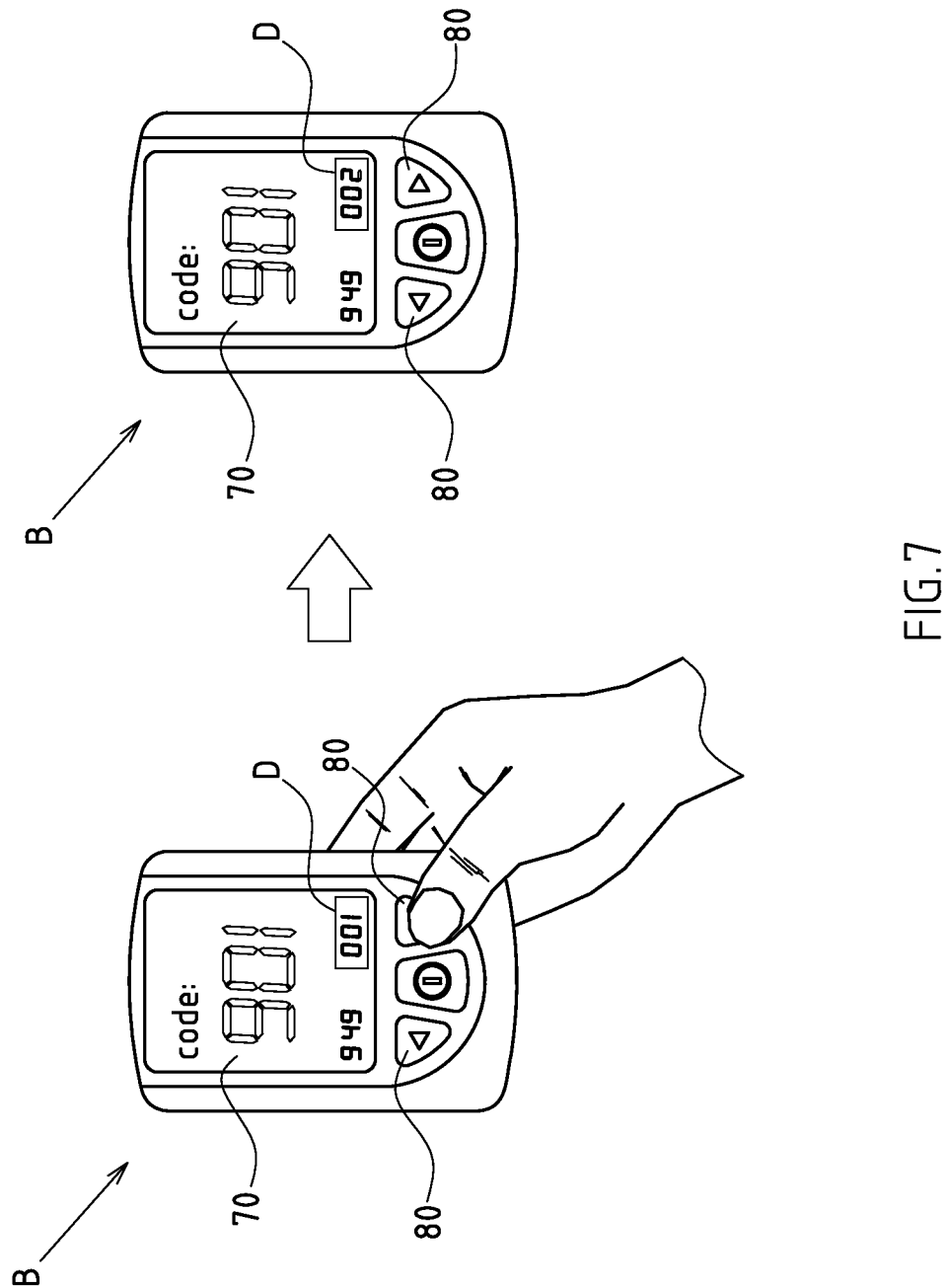
FIG. 7 is a schematic view of the preferred embodiment of the present invention with use of input means by the test value adjustment mode.

Referring also to FIG. 7, said test value adjustment mode could also be implemented by means of input, namely, an adjustment button 80 (a push button or a rotary button) is set on the electrochemical tester B. Hence, the users could adjust or change the operational parameters of the test value correction procedure by using the adjustment button 80. As shown by the symbolic letters of a parameter frame D in the measurement display 70 of the electrochemical tester B, after correction of test value by the adjustment button 80, the symbolic letters shown by a parameter frame D in the electrochemical tester B are switched to the symbolic letters represented by the test value correction procedure unique to the tested animal.

In addition to the preferred embodiments shown in FIGS. 6 and 7, said test value adjustment mode could also be implemented by code scanning, namely, a code scanning slot is preset on the electrochemical tester B, and a code scanning card for adjustment is also provided. An adjustment code is built into the code scanning card for adjustment, enabling to read the code scanning card for adjustment in the code scanning slot, so as to change the operational parameters of the test value correction procedure.

Figure 8:
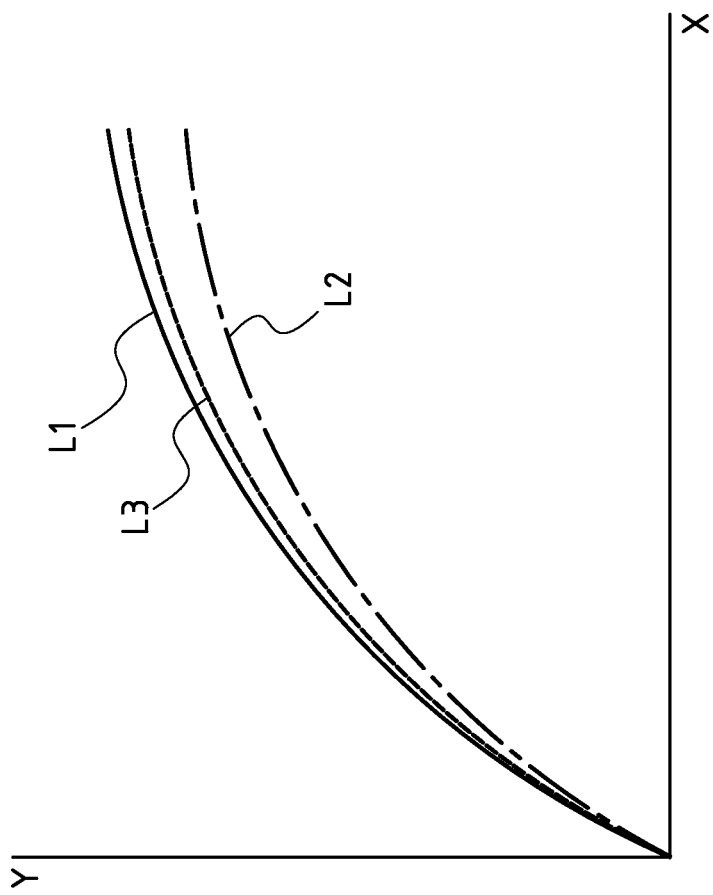
FIG. 8 is a curve comparison chart of results among the tests of the present invention, special lab tests and electrochemical tests.

Referring also to FIG. 8, a parameter adjustment mode is used to adjust the operational parameters of the test value correction procedure unique to the electrochemical tester, and adapt them to the test mode of the species of the tested animals. Under the same conditions of the tested animals, if assuming the curve L1 in FIG. 8 means the test result obtained by special lab tests, and common electrochemical test means are introduced, the test results have a bigger error as indicated by curve L2 in FIG. 8. When the electrochemical test means of the present invention with parameter adjustment mode are introduced, the test results are in consistency with or close to the results from special lab tests as indicated by curve L3 in FIG. 8, so accurate test results of animal blood ketone could be obtained in a simple way to meet the relevant customer demands.

I claim:

1. A method for testing for a ketone number of a non-human animal specimen, the method comprising:
   setting up a test parameter datasheet by data modeling based on a comparative difference of test results obtained in a lab to tests obtained by electrochemical testing according to a type of the animal specimen, and drawing the test parameter datasheet based on the test results;
   dripping the specimen onto a sensing end of an electrochemical specimen;
   preparing an electrochemical tester provided with a measurement slot, said electrochemical tester having a test value correction procedure incorporated therein or input thereto;
   adjusting operational parameters unique to the test value correction procedure of the electrochemical tester so as to adapt to a test mode of a species of the tested animal, the test value correction procedure being expressed by y=ax+b where x and y represent respectively two axial directions in a curve graph of the ketone number and where a and b represent a pair of parameters affecting the curve, a and b being obtained from data in said test parameter datasheet; and
   inserting said sensing end of said electrochemical test specimen into said measurement slot of said electrochemical tester, said electrochemical tester displaying the ketone number of the animal specimen.

2. The method of claim 1, the wherein the tested animal specimen is selected from the group consisting of cattle, sheep, horses, dogs, cats and pigs.

3. The method of claim 1, further comprising:
   categorizing the tested animal specimen by size or age.

4. The method of claim 1, wherein the tested animal specimen is selected from the group consisting of blood, body fluid, urine, saliva, tissue fluid, lymph and milk.

5. The method of claim 1, said electrochemical test specimen having a laminar insulation substrate having an insertion end and a sensing end, said electrochemical test specimen having an electrode unit with a detection zone and a reaction zone, said detection zone positioned so as to correspond to said insertion end, said reaction zone positioned so as to correspond to said sensing end, said electrochemical test specimen having a reaction portion positioned at said sensing end so as to correspond to said reaction zone, said reacion portion provided with a specimen inlet and a chemical reaction zone, said measurement slot of said electrochemical tester receiving said insertion end of said electrochemical test specimen, said electrochemical tester having a voltage generator for generating a present voltage and a detection processor for detecting current signals generated by said electrochemical test specimen containing the animal specimen over a period of time, said electrochemical tester for correlating the current signals with a concentration of the animal specimen, said electrochemical tester having a display for showing measurement results.

6. The method of claim 1, further comprising:
   providing a test value adjustment mode by an adjustment specimen inserted into an insertion portion of said measurement slot;
   building an adjustment code into the adjustment specimen such that the adjustment code can be read when the adjustment specimen is inserted into the electrochemical tester so as to change operational parameters of a test value correction procedure.

7. The method of claim 1, further comprising:
   implementing a test value adjustment mode by an adjustment button positioned on said electrochemical tester; and
   adjusting operational parameters of a test value correction procedure by using said adjustment button.

8. The apparatus of claim 1, further comprising:
   implementing a test value adjustment mode by code scanning in which a code scanning slot is set on said electrochemical tester;
   building an adjustment code onto a code scanning card;
   introducing said code scanning card into said code scanning slot so as to change operational parameters of a test value correction procedure.

9. The method of claim 1, wherein said test parameter datasheet is selected from a group consisting of cards, electronic codes and electronic files.

* * * * *